United States Patent [19]
Stewart et al.

[11] Patent Number: 6,130,180
[45] Date of Patent: Oct. 10, 2000

[54] CATALYST FOR THE POLYMERIZATION OF ALPHA-OLEFINS CONTAINING SUBSTITUTED AMINO SILANE COMPOUNDS

[75] Inventors: Constantine A. Stewart; Eric J. Evain, both of Wilmington, Del.

[73] Assignee: Montell North America Inc., Wilmington, Del.

[21] Appl. No.: 08/996,854

[22] Filed: Dec. 23, 1997

[51] Int. Cl.⁷ .............................. B01J 31/00; C08F 4/656
[52] U.S. Cl. ..................... 502/124; 502/119; 502/121; 502/123; 502/125; 502/126; 502/127; 544/229; 546/14; 556/413
[58] Field of Search ...................... 502/119, 123, 502/124, 125, 126, 127; 528/121; 544/229; 546/14; 556/413

[56] References Cited

U.S. PATENT DOCUMENTS

| | | | |
|---|---|---|---|
| 4,180,636 | 12/1979 | Hirota et al. | 526/125 |
| 4,242,479 | 12/1980 | Yokota et al. | 526/124 |
| 4,347,160 | 8/1982 | Epstein et al. | 252/429 |
| 4,352,917 | 10/1982 | Tripp | 528/26 |
| 4,382,019 | 5/1983 | Greco | 252/429 |
| 4,435,550 | 3/1984 | Ueno et al. | 526/73 |
| 4,442,276 | 4/1984 | Kashiwa et al. | 526/125 |
| 4,465,782 | 8/1984 | McKenzie | 502/104 |
| 4,472,524 | 9/1984 | Albizzati | 502/113 |
| 4,473,660 | 9/1984 | Albizzati et al. | 502/124 |
| 4,522,930 | 6/1985 | Albizzati et al. | 502/124 |
| 4,530,912 | 7/1985 | Pullukat et al. | 502/104 |
| 4,560,671 | 12/1985 | Gross et al. | 502/105 |
| 4,581,342 | 4/1986 | Johnson et al. | 502/119 |
| 4,657,882 | 4/1987 | Karayannis et al. | 502/115 |
| 5,102,842 | 4/1992 | Smith et al. | 502/124 |
| 5,401,566 | 3/1995 | Magee et al. | 428/266 |

FOREIGN PATENT DOCUMENTS

| | | |
|---|---|---|
| 0 045 976 A2 | 2/1982 | European Pat. Off. . |
| 0 045 977 B1 | 2/1982 | European Pat. Off. . |
| 0 658 577 B1 | 6/1995 | European Pat. Off. . |
| 0 841 348 A2 | 5/1998 | European Pat. Off. . |
| 7-118320 | 5/1995 | Japan . |

*Primary Examiner*—Elizabeth D. Wood

[57] ABSTRACT

An aminosilane of the formula:

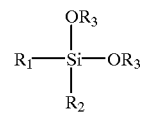

where $R_1$ is a linear or branched $C_{1-22}$ alkyl or $C_{3-22}$ cycloalkyl, which may be substituted with at least one halogen atom; $R_2$ is a bis(linear or branched $C_{1-22}$ alkyl or $C_{3-22}$ cycloalkyl)amino, a substituted piperidinyl, a substituted pyrrolidinyl, decahydroquinolinyl, 1,2,3,4-tetrahydroquinolinyl or 1,2,3,4-tetrahydroisoquinolinyl, with the substituent selected from the group consisting of $C_{1-8}$ alkyl, pheny. $C_{1-8}$ linear or branched alkylsubstituted phenyl and trimethylsilyl, with the proviso that when the substituent is $C_{1-8}$ alkyl, there must be at least two such substituent groups present and $R_1$ must contain halogen; and $R_3$ is a linear or branched $C_{1-8}$ alkyl or $C_{3-8}$ cycloalkyl. The aminosilane may be reacted with an aluminum-alkyl compound and a solid component comprising a titanium compound having at least one titanium-halogen bond and an electron donor, both supported on an activated anhydrous magnesium dihalide, to form a catalyst for polymerization of olefins.

16 Claims, No Drawings

CATALYST FOR THE POLYMERIZATION OF ALPHA-OLEFINS CONTAINING SUBSTITUTED AMINO SILANE COMPOUNDS

BACKGROUND OF THE INVENTION

This invention relates to Ziegler-Natta catalyst systems which use an amino substituted silane electron donor as a co-catalyst component. The olefin polymers produced with such catalyst systems exhibit a desirable combination of high isotacticity and high polydispersity index.

The isotacticity of a polymer is important in determining its suitability for a given application. Isotacticity is often measured by determining the weight percent of xylene-soluble polymer at room temperature (XSRT) and subtracting this from one hundred percent. A high isotacticity of greater than 90 is preferred and greater than 95 is most preferred.

Polydispersity index (P.I.) is a measurement of the molecular weight distribution of a polymer. A broad molecular weight range distribution (a high P.I.>4.0) provides improved melt strength, which is advantageous in thermoforming, film, and fiber formation operations. A high P.I. of 4.0 is indicative of a broad molecular weight distribution. Preferably the P.I. is>4.5, most preferably 5.0 or greater.

Organosilane compounds have been used in catalyst systems (1) as an electron donor in the solid catalyst component comprising a halogen-containing Ti compound supported on an anhydrous activated Mg-dihalide compound and (2) as an electron donor with the co-catalyst component comprising an organometallic compound. Typically they are organosilane compounds having Si—OR, Si—OCOR or Si—NR$_2$ bonds, where R is alkyl, alkenyl, aryl, arylalkyl or cycloalkyl having 1 to 20 carbon atoms and Si as the central atom. Such compounds are described in U.S. Pat. Nos. 4,180,636; 4,242,479; 4,347,160; 4,382,019; 4,435,550; 4,442,276; 4,465,782, 4,473,660; 4,530,912 and 4,560,671, where they are used as electron donors in the solid catalyst component; and in U.S. Pat. Nos. 4,472,524, 4,522,930, 4,560,671, 4,581,342, 4,657,882 and European patent applications 45976 and 45977, where they are used as electron donors with the co-catalyst.

U.S. Pat. No. 5,102,842 discloses trifluoropropyl-substituted silanes which may also contain a piperidinyl or pyrrolidinyl ring, such as 3,3,3-trifluoropropyl (pyrrolidyl)-dimethoxysilane and 3,3,3-trifluoropropyl (4-methylpiperidyl)dimethoxysilane. Even more recently, European Patent Publication No. 658,577 teaches that fiber prepared from propylene homopolymers polymerized using trifluoropropyl(alkyl)dimethoxysilane has a lower bonding temperature and wider bonding temperature window than fibers of propylene homopolymer polymerized using catalysts having conventional electron donors such as phenyltriethoxysilane, dicyclopentyldimethoxysilane and diphenyldimethoxysilane.

An object of this invention is to provide novel aminosilanes useful as electron donors in olefin polymerization catalyst systems. Another object of the invention is to provide an improved catalyst system which produces olefin polymers having a desirable combination of high isotacticity and high polydispersity index.

SUMMARY OF THE INVENTION

In one aspect, the present invention relates to aminosilane compounds conforming to the following formula:

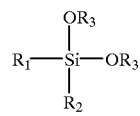

wherein

R$_1$ is a linear or branched C$_{1-22}$ alkyl or C$_{3-22}$ cycloalkyl, which may be substituted with at least one halogen atom;

R$_2$ is a bis(linear or branched C$_{1-22}$ alkyl or C$_{3-22}$ cycloalkyl) amino, a substituted piperidinyl, a substituted pyrrolidinyl, decahydroquinolinyl, 1,2,3,4-tetrahydroquinolinyl or 1,2,3,4-tetrahydroisoquinolinyl, with the substituent selected from the group consisting of linear or branched C$_{1-8}$ alkyl, phenyl, linear or branched C$_{1-8}$ alkyl substituted phenyl and trimethylsilyl, with the proviso that when the substituent is C$_{1-8}$ alkyl, there must be at least two such substituent groups present and R$_1$ must contain halogen; and R$_3$ is a linear or branched C$_{1-8}$ alkyl or C$_{3-8}$ cycloalkyl.

In a second aspect, the present invention relates to a catalyst for the polymerization of olefins, comprising the reaction product of:

(A) an aluminum alkyl compound;

(B) aminosilane compounds described above, and (C) a solid component comprising a titanium compound having at least one titanium-halogen bond and an electron donor, both supported on an activated anhydrous magnesium dihalide compound.

DETAILED DESCRIPTION OF THE PREFERRED EMBODIMENTS

As summarized above, the aminosilane compounds of the present invention conform to the following formula:

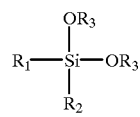

wherein

R$_1$ is a linear or branched C$_{1-22}$ alkyl or C$_{3-22}$ cycloalkyl, which may be substituted with at least one halogen atom;

R$_2$ is a bis(linear or branched C$_{1-22}$ alkyl or C$_{3-22}$ cycloalkyl) amino, a substituted piperidinyl, a substituted pyrrolidinyl, decahydroquinolinyl, 1,2,3,4-tetrahydroquinolinyl or 1,2,3,4-tetrahydroisoquinolinyl, with the substituent selected from the group consisting of linear or branched C$_{1-8}$ alkyl phenyl, linear or branched C$_{1-8}$ alkyl substituted phenyl and trimethylsilyl, with the proviso that when the substituent is C$_{1-8}$ alkyl, there must be at least two such substituent groups present and R$_1$ must contain halogen; and R$_3$ is a linear or branched C$_{1-8}$ alkyl or C$_{3-8}$ cycloalkyl.

Preferably, R$_1$ is 3,3,3-trifluoropropyl, and R$_3$ is methyl or ethyl. Illustrative compounds coming within these preferred definitions include 3,3,3-trifluoropropyl(2-trimethylsilylpiperidinyl) dimethoxysilane;

3,3,3-trifluoropropyl(2-trimethylsilylpyrrolidinyl) dimethoxysilane;

3,3,3-trifluoropropyl(2-(3-methylphenyl)piperidinyl) dimethoxysilane;

3,3,3-trifluoropropyl(2-(3-methylphenyl)pyrrolidinyl) dimethoxysilane;

3,3,3-trifluoropropyl(1,2,3,4-tetrahydroquinolinyl) dimethoxysilane;

3,3,3-trifluoropropyl(1,2,3,4-tetrahydroisoquinolinyl) dimethoxysilane;

3,3,3-trifluoropropyl(decahydroquinolinyl) dimethoxysilane;

3,3,3-trifluoropropyl(bis(2-ethylhexyl)amino) dimethoxysilane; and 3,3,3-trifluoropropyl(cis-2,6-dimethylpiperidinyl) dimethoxysilane.

The aminosilanes may be prepared by a multistep synthesis route. The first step is a reaction between the anion from a $C_{1-22}$ alkane or halide-substituted alkane and a commercially available silane such as tetraalkylorthosilicate ($SiOR_4$) or tetrachlorosilane. When tetrachlorosilane is used, an (alkyl)trichlorosilane or (halide-substituted alkyl) trichlorosilane results. This is converted to the corresponding (alkyl)trialkoxysilane or (halide-substituted alkyl) trialkoxysilane by treatment with the appropriate alkoxide (e.g.; methoxide or ethoxide). When a tetraalkylorthosilicate is used, the (alkyl)trialkoxysilane or (halide-substituted alkyl)trialkoxysilane is prepared directly.

The final step is a substitution reaction between the (alkyl)trialkoxysilane or (halide-substituted alkyl) trialkoxysilane and a substituted secondary or cyclic amine. The amine-anion is generated by treatment with either n-butyl lithium or isopropylmagnesium chloride. The anion is then allowed to react with the (alkyl)trialkoxysilane or (halide-substituted alkyl)trialkoxysilane to produce the aminosilane.

It is necessary to use a protecting group to prepare certain amines. A suitable protecting group is tert-butylcarbamate ("BOC") which was used to prepare 2-trimethylsilylpiperidine, 2-trimethylsilylpyrollidine, 2-(3-methylphenyl)piperidine, and a 2-(3-methylphenyl) pyrrolidine. The BOC group was attached by generating the anion from either piperidine or pyrrolidine using sodium hydride in tetrahydrofuran. This solution was cooled to 5° C. and a slight excess of di-tert-butyldicarbonate added. After two hours, the solution was poured into saturated sodium bicarbonate and the layers separated. The organic layer was dried over magnesium sulfate and the solvent removed by rotary evaporation. Distillation at reduced pressure provided either piperidinyl-N-tert-butylcarbamate (bp 95° C., 3 mm Hg, 89% yield) or pyrrolidinyl-N-tert-butylcarbamate (bp 69° C., 1 mm Hg, 95% yield).

The aminosilanes of the present invention may be reacted with an aluminum alkyl compound (A) and a solid component (C) comprising a titanium compound having at least one titanium-halogen bond and an electron donor, both supported on an activated anhydrous magnesium dihalide, to form catalysts suitable for olefin polymerization.

The Al-alkyl compounds forming component (A), which are non-halogen containing, include: Al-trialkyl, such as Al-triethyl, Al-triisopropyl, Al-triisobutyl, Al-dialkyl hydrides, such as Al-diethyl hydride, and compounds containing two or more Al atoms linked to each other through oxygen, nitrogen or sulfur hetero-atoms, such as:

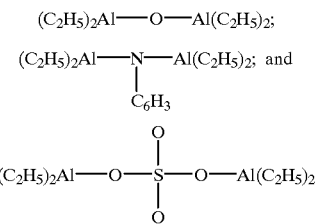

Preferably, the Al-alkyl compound is Al-triethyl.

In the solid component (C), suitable examples of the titanium compound having at least a Ti-halogen bond are Ti-tetrahalides, in particular, $TiCl_4$. However, alkoxy halides can also be used.

The electron donor compounds employed in component (C) include alkyl, aryl and cycloalkyl esters of aromatic acids, especially benzoic acid or phthalic acid and their derivatives. Specific examples include ethyl benzoate, n-butyl benzoate, methyl p-toluate, diisopropylphthalate, di-n-butylphthalate, diisobutylphthalate and dioctylphthalate. In addition to the above esters, alkyl or alkaryl ethers, ketones, mono- or polyamines, aldehydes and phosphorus compounds, such as phosphines and phosphoramides, can also be used as the electron donor. The phthalic acid esters are most preferred.

The active anhydrous magnesium dihalides forming the support of component (C) are the Mg dihalides showing in the X-ray powder spectrum of component (C) a broadening of at least 30% of the most intense diffraction line which appears in the powder spectrum of the corresponding dihalide having 1 $m^2/g$ of surface area or are the Mg dihalides showing an X-ray powder spectrum in which said most intense diffraction line is replaced by a halo with an intensity peak shifted with respect to the interplanar distance of the most intense line and/or are the Mg dihalides having a surface area greater than 3 $m^2/g$.

The measurement of the surface area of the Mg dihalides is made on component C) after treatment with boiling $TiCl_4$ for 2 hours. The value found is considered as surface area of the Mg dihalide.

The Mg dihalide may be preactivated, may be activated in situ during the titanation, may be formed in situ from a Mg compound, which is capable of forming Mg dihalide when treated with a suitable halogen-containing transition metal compound, and then activated, or may be formed from a Mg dihalide $C_{1-3}$ alkanol adduct wherein the molar ratio of $MgCl_2$ to alcohol is 1:1 to 1:3, such as $MgCl_2 \cdot 3ROH$.

Very active forms of Mg dihalides are those showing an X-ray powder spectrum in which the most intense diffraction line appearing in the spectrum of the corresponding halide having 1 $m^2/g$ of surface area is decreased in relative intensity and broadened to form a halo or are those in which said most intense line is replaced by a halo having its intensity peak shifted with respect to the interplanar distance of the most intense line. Generally, the surface area of the above forms is higher than 30–40 $m^2/g$ and is comprised, in particular, between 100–300 $m^2/g$.

Active forms are also those derived from the above forms by heat-treatment of component (C) in inert hydrocarbon solvents and showing in the X-ray spectrum sharp diffraction lines in place of halos. The sharp, most intense line of these forms shows, in any case, a broadening of at least 30% with respect to the corresponding line of Mg dihalides having 1 $m^2/g$ of surface area.

Preferred Mg dihalides are $MgCl_2$ and $MgBr_2$ and the most preferred is $MgCl_2$. The content in water of the halides is generally less than 1% by weight.

By Ti halides or Ti alkoxy halides and electron donors supported on active Mg dihalide is meant the above compounds which may be chemically or physically fixed on e support and not extractable from component (C) by treatment of the same with boiling 1,2-dichloroethane for 2 hours.

Component (C) can be made by various methods. One method consists of co-grinding the Mg dihalide and the electron donor compound until the product, after extraction with Al-triethyl under standard conditions, shows a surface area higher than 20 m$^2$g, as set forth above for the spectrum of the Mg dihalide, and thereafter reacting the round product with the Ti compound.

Other methods of preparing the solid catalyst component (C) are disclosed in U.S. Pat. Nos. 4,220,554; 4,294,721; 4,315,835 and 4,439,540, the methods of which are incorporated herein by reference.

In all of the above methods, component (C) contains a Mg dihalide present in the active form as set forth above.

Other known methods which lead to the formation of Mg dihalide in active form or to Ti-containing Mg di-halide supported components, in which the dihalide is present in active form, are based on the following reactions:

(i) reaction of a Grignard reagent or of a MgR$_2$ compound (R being a hydrocarbyl radical) or of complexes of said MgR$_2$ compounds with Al trialkyl, with halogenating agents as AlX$_3$ or AlR$_m$X$_n$ compounds (X is halogen, R is a hydrocarbyl, m+n=3), SiCl$_4$ or HSiCl$_3$;

(ii) reaction of Grignard compound with a silanol or polysiloxane, H$_2$O or with an alcohol and further reaction with a halogenating agent or with TiCl$_4$;

(iii) reaction of Mg with an alcohol and a halogen halide acid, or of Mg with a hydrocarbyl halide and an alcohol;

(iv) reaction of MgO with Cl$_2$ or AlCl$_3$;

(v) reaction of MgX$_2$.nH$_2$O (X=halogen and n is 1–3) with a halogenating agent or TiCl$_4$; or (vi) reaction of Mg mono or dialkoxides or Mg carboxylates with a halogenating agent.

In component (C), the molar ration between the Mg dihalides and the halogenated Ti compound supported thereon is between 1 and 500 and the molar ratio between said halogenated Ti compound and the electron donor supported on the Mg dihalide is between 0.1 and 50.

The catalyst, i.e., components (A), (B) and (C) can be added to the polymerization reactor by separate means substantially simultaneously, regardless of whether the monomer is already in the reactor, or sequentially if the monomer is added to the polymerization reactor later. It is preferred to premix components (A) and (B), then contact said premix with component (C) prior to the polymerization for from 3 minutes to about 10 minutes at ambient temperature.

The olefin monomer can be added prior to, with or after the addition of the catalyst to the polymerization reactor. It is preferred to add it after the addition of the catalyst.

Hydrogen can be added as needed as a chain transfer agent for reduction in the molecular weight of the polymer. It is possible to achieve a melt flow rate of over 1500 g/10 minutes using an appropriate amount of hydrogen and proper selection of the aminosilane compound. See Example IX below.

The polymerization reactions can be done in slurry, liquid or gas phase processes, or in a combination of liquid and gas phase processes using separate reactors, all of which can be done either by batch or continuously.

The polymerization is generally carried out at a temperature of from 40–90° C. and at atmospheric pressure or at higher pressure.

The catalysts may be precontacted with small quantities of olefin monomer prepolymerization), maintaining the catalyst in suspension in a hydrocarbon solvent and polymerizing at a temperature of 60° C. or below for a time sufficient to produce a quantity of polymer from 0.5 to 3 times the weight of the catalyst.

This prepolymerization also can be done in liquid or gaseous monomer to produce, in this case, a quantity of polymer up to 1000 times the catalyst weight.

Suitable alpha-olefins which can be polymerized by this invention include olefins of the formula CH$_2$=CHR, where R is H or C$_{1-10}$ straight or branched alkyl, such as ethylene, propylene, butene-1, pentene-1,4-methylpentene-1 and octene-1.

The following examples are shown to illustrate the invention and are not intended to define the scope thereof.

Unless otherwise indicated all parts and percentages in this application are by weight.

EXAMPLES

Preparation of Electron Donor Compounds
General Procedures:

The purity of all reagents was confirmed by either chromatographic or spectrophotometric analysis. Where appropriate, reagents were purified prior to use. All non-aqueous reactions were performed under an atmosphere of dry nitrogen or argon using glassware that was dried under vacuum while heated. Air and moisture sensitive solutions were transferred via syringe or stainless steel cannula. Boiling points and melting points were uncorrected.

NMR spectra were recorded on a Varian Unity 300 spectrometer operating at 300 MHz and are referenced internally to either tetramethylsilane or residual proton impurities. Data for $^1$H are reported as follows: chemical shift, (, ppm), multiplicity (s-singlet; d-doublet; t-triplet; q-quartet; qn-quintet; m-multiplet), integration. Data for $^{13}$C NMR are reported in terms of chemical shift (δ, ppm). Infrared spectra were reported on a BioRad FT430 series mid-IR spectrometer using KBr plates and are reported in terms of frequency of absorption (v, cm$^1$).

GC analyses were conducted using a Hewlett Packard model 6890 chromatograph using flame ionization detection ("FID") coupled to a model HP6890 integrator. In a typical analysis of 1.0 μL was injected into a 250° C. injector (50:1 split ratio; 10 psi column head pressure, 106 mL/min split flow; 111 mL/min total flow). Helium as used as a carrier gas through an Alltech Heliflex AT-1 column (30 m×0.32 mm×0.3 m). The initial temperature was held at 50° C. for two minutes then increased at 10° C./min to a final temperature of 300° C. The FID detector was held at 300° C. (40 mL/min H$_2$; 400 mL/min air; constant make-up mode using 30 mL/min He).

Two GC/MS systems were used. One system was a Hewlett Packard model 5890 GC coupled to a Hewlett Packard model 5970 mass selective ("MSD"). In a typical analysis, 2.0 μL of sample was injected into a 290° C. splitless injection port. Helium was used as the carrier gas through an HP-1 (Hewlett Packard, 25 m×0.33 mm×0.2 μm). The initial temperature was held at 75° C. for four minutes. The column was warmed at 10° C./min. MSD acquisition was 10-800 AMU. The spectra are reported as m/z (relative abundance).

The second GC/MS system was a Hewlett Packard model 6890 GC coupled to a Hewlett Packard model 5973 mass selective detector. In a typical analysis, 1.0 μL of sample was injected into a 290° C. split/splitless injection port. Helium was used as the carrier gas through an HP-5 (Hewlett Packard, 30 m×0.25 mm×0.25 μm). The initial temperature was held at 50° C. for four minutes. The column was warmed at 10° C./min. Mass acquisition was 10-800 AMU. The spectra are reported as m/z (relative abundance).

Example I 3,3,3-Trifluoropropyl(2-trimethylsilylpiperidinyl) dimethoxysilane 2-Trimethylsilylpiperidinyl-N-tert-butylcarbamate—A 1000 mL flask was charged with piperidinyl-N-tert-butylcarbamate (25.0 g, 135 mmol), tetramethylethylenediamine ("TMEDA," 44 mL, 290 mmol) and anhydrous ether (300 mL). The contents were cooled to −78° C. Sec-butyl lithium (125 mL of 1.3 M solution in cyclohexane, 162 mmol) was added over 25 minutes. The contents were stirred for 3.5 hours while maintaining the reaction temperature at −78° C. Chlorotrimethylsilane ("TMS-Cl", 21.0 mL, 165 mmol) was added over 15 minutes and the contents allowed to warm to room temperature and stirred for 18 hours. The solution was poured into dilute hydrochloric acid (400 mL, 0.2 N). The layers were separated and the organic layer was washed with 0.2 N HCl (3×100 mL) and dried ($MgSO_4$). Removal of solvent via rotary evaporation provided 53.3 g of 2-trimethylsilylpiperidinyl-N-tert-butylcarbamate: $C_{13}H_{27}NO_2Si$ (mw=257.44); MS:m/z (relative abundance) 200 (18.2), 186 (40.2), 156 (47.7), 128 (26.9), 84 (45.5), 73 (100), 57 (87.3).

2-Trimethylsilylpiperidine—A 1000 mL flask was charged with 600 mL ethyl acetate and chilled to 5° C. Anhydrous hydrogen chloride (>99%) was bubbled through the ethyl acetate for 15 minutes. The ice bath was removed and the 2-trimethylsilylpiperidinyl-N-tert-butylcarbamate (107 g, 416 mmol) was added. The solution was stirred for 18 hours. The product was extracted into water (3×200 mL), the layers separated, and the combined aqueous layers washed with ether (200 mL). The aqueous portion was brought to pH 14 using 45% (wt/v) potassium hydroxide and extracted with ether (3×150 mL). The combined organic portions were dried ($MgSO_4$) and the solvent removed via rotary evaporation. Distillation at reduced pressure (bp 29° C., 0.5 mmHg) provided 2-trimethylsilylpiperidine (17.0 g, 108 mmol, 26% yield, 97.4% purity by GC); $C_8H_{19}NSi$ (mw=157.33); $^1H$ NMR: ($CDCl_3$) δ 3.08 (m, 2H), 2.55 (m, 2H), 2.01 (m, 2H) 1.79 (s, 2H), 1.61–0.80 (m, 11H); $^{13}C$ NMR: ($CDCl_3$) δ 49.0, 48.4, 27.6, 27.0, 26.2, 4.4; IR (capillary film) v 2926, 2851, 1440, 1258, 1247, 918, 888, 833, 765, 737, 696; MS: m/z (relative abundance) 128 (7.5), 84 (100), 73 (13.8), 56 (17.7), 28 (10.1).

3,3,3-Trifluoropropyl(2-trimethylsilylpiperidinyl) dimethoxysilane—A 500 mL round bottomed flask was charged with tetrahydrofuran (300 mL) and isopropyl-magnesium chloride (21.5 mL of a 2.0 M solution in THF, 43 mmol). The contents were cooled to 15° C. 2-Trimethylsilylpiperidine (44.5 mmol) was added over fifteen minutes via pressure equalizing addition funnel. The cold bath was removed and the contents stirred for two hours. 3,3,3-Trifluoropropyltrimethoxysilane (39.5 mmol) was added via pressure equalizing addition funnel. The contents were brought to reflux (65–70° C.) for two hours, and reaction progress was monitored by GC. Isolation was accomplished by removing the THF via rotary evaporation, taking the residue up in ether (250 mL), filtration and ether removal via rotary evaporation. Purification was accomplished by distillation to provide 3,3,3-trifluoropropyl(2-trimethylsilylpiperidinyl)dimethoxysilane (33.5 mmol; 85.0% yield). $C_{13}H_{28}NO_2SiF_3$ (mw=343.53); $^1H$ NMR: ($CDCl_3$) δ 3.5 (s, 6H), 3.1–2.9 (m, 1H), 2.8–2.6 (m, 2H), 2.2–2.0 (m, 2H), 1.8–1.35 (m, 5H), 1.32–1.15 (m, 1H), 0.9–0.7 (m, 2H), 0.1 (s, 9H); $^{13}C$ NMR: ($CDCl_3$) 127.7 (quartet J=275 Hz), 50.1, 42.6, 42.2, 28.0 (quartet J=30 Hz), 27.8, 23.4, 3.0, 0.2, −4.2; MS: m/z (relative abundance) 328 (1.2), 270 (100), 246 (2.2), 155 (6.5), 125 (12.0), 84 (21.5).

Example II 3,3,3-Trifluoropropyl(2-trimethylsilylpyrrolidinyl) dimethoxysilane 2-trimethylsilylpyrrolidinyl-N-tert-butylcarbamate—A 1000 mL flask was charged with pyrrolidinyl-N-tert-butylcarbamate (23.2 g, 136 mmol), tetramethylethylenediamine (44 mL, 290 mmol) and anhydrous ether (300 mL), and cooled to −78° C. Sec-butyl lithium (125 mL of 1.3 M solution in cyclohexane, 162 mmol) was added over 25 minutes. The reaction contents were stirred for 3.5 hours while maintaining the temperature at −78° C. Chlorotrimethylsilane (21.0 mL, 165 mmol) was added over 15 minutes. The contents were allowed to warm to room temperature and stirred for 18 hours. The solution was poured into dilute hydrochloric acid (750 mL, 0.2 N HCl). The layers were separated and the organic layer was washed with 0.2 N HCl (3×200 mL), brine (1×250 mL), and dried ($MgSO_4$). Removal of solvent via rotary evaporation provided 93 g of crude product. Distillation under reduced pressure (85–92° C., 1.8 mmHg) provided 45.9 g (189 mmol, 70% yield) of 2-trimethylsilylpyrrolidinyl-N-tert-butylcarbamate; $C_{12}H_{25}NO_2Si$ (mw=243.42).

2-Trimethylsilylpyrrolidine—A 1000 mL flask was charged with 600 mL ethyl acetate and chilled to 5° C. Anhydrous hydrogen chloride gas (99+%) was bubbled through the ethyl acetate for 15 minutes. The HCl feed was stopped, the ice bath removed, and the 2-trimethylsilylpyrrolidinyl-N-tert-butylcarbamate (45.9 g, 189 mmol) added. The solution was allowed to stir for 18 hours. Water (250 mL) was added to the solution. The layers were separated and the product was extracted into water (3×200 mL). The aqueous portion was adjusted to pH 14 using 45% (wt/v) potassium hydroxide. Ether was added (200 mL), the layers separated, and the aqueous layer extracted into ether (3×150 mL). The combined organic portions were dried ($MgSO_4$) and the solvent removed via rotary evaporation. Distillation at reduced pressure (25° C., 1.5 mmHg) provided 2-trimethylsilylpyrrolidine (16.0 g, 112 mmol, 64% yield, >99% purity); $C_{17}H_{11}NSi$ (mw= 143.30); $^{13}C$ NMR: δ 49.0, 48.9, 28.1, 26.7, −3.3, −3.6, −4.0; IR (capillary film) v 2952, 2866, 2823, 2752, 1423, 1247, 1069, 936, 892, 837, 747, 692, 622; MS: m/z (relative abundance) 115 (11.9), 100 (14.9), 73 (10.0), 70 (100), 43 (12.4), 28 (13.2).

3,3,3-Trifluoropropyl(2-trimethylsilylpyrrolidinyl) dimethoxysilane—A 500 mL round bottomed flask was charged with tetrahydrofuran (300 mL) and isopropyl-magnesium chloride (28.25 mL of a 2.0 M solution in THF, 56.5 mmol). The contents were cooled to 15° C. 2-Trimethylsilylpyrrolidine (58.0 mmol) was added over fifteen minutes via pressure equalizing addition funnel. The cold bath was removed and the contents stirred for two hours. 3,3,3-Trifluoropropyltrimethoxysilane (51.3 mmol) was added via pressure equalizing addition funnel. The contents were brought to reflux (65–70° C.) for two hours, and reaction progress was monitored by GC. Isolation was accomplished by removing the THF via rotary evaporation, taking the residue up in ether (250 mL), filtration and ether removal via rotary evaporation. Purification was accomplished by distillation to provide 3,3,3-trifluoropropyl(2-trimethylsilylpyrrolidinyl)dimethoxysilane (46.7 mmol; 91% yield). $C_{12}H_{26}NO_2Si_2F_3$ (mw=329.51); $^1H$ NMR: ($CDCl_3$) δ 3.50 (s, 3H), 3,45 (s, 3H), 3.25–3.10 (m, 1H), 2.90–2.80 (m, 1H), 2.80–2.65 (m, 1H), 2.20–1.50 (m, 6H), 0.85–0.75 (m, 2H), −0.05 (s, 9H); $^{13}C$ NMR: ($CDCl_3$) δ 129.6 (quartet J=275), 50.1, 49.0, 47.6, 46.7, 28.2 (quartet J=30), 28.0, 27.5, 2.9, −2.7; $^{29}Si$ NMR: ($CDCl_3$) δ 2.07, −34.74; MS: m/z (relative abundance) 314 (1.5), 256 (100), 232 (1.7), 155 (3.8), 125 (3.6) 70 (4.2).

Example III 3,3,3-Trifluoropropyl(2-(3-methylphenyl)-piperidinyl) dimethoxysilane (2-(3-Methyiphenyl)piperidinyl)-N-tert-butylcarbamate—A 500 mL flask was charged with piperidinyl-N-tert-butylcarbamate (18.5 g, 100×10$^2$ mmol), tetramethylethylenediamine (33 mL, 220 mmol), and THF (200 mL). The contents were cooled to −78° C. Sec-butyl lithium (93 mL of 1.3 M solution in cyclohexane, 120 mmol) was added over 15 minutes. The reaction was stirred at −78° C. for 3.5 hours. A 1000 mL flask was charged with THF (200 mL), 3-iodotoluene (25.7 mL, 2.00×10$^2$ mmol), copper (I) cyanide (0.896 g, 1.00×10$^2$ mmol), and bis (triphenylphosphine)palladium chloride (3.5 g, 5.0 mmol). The contents were cooled to −78° C. The piperidinyl-N-tert-butylcarbamate anion was transferred into the iodotoluene solution via cannula. The reaction was allowed to stir for 18 hours and then heated to reflux (75° C.) for another 18 hours. The cooled contents were added to water (200 mL), the layers separated, and the aqueous layer extracted with ether (2×150 mL). The combined organic portions were washed with brine (3×150 mL) and dried ($MgSO_4$). Removal of solvent by rotary evaporation provided 59.5 g of crude 2-(3-methylphenyl)-piperidinyl-N-tert-butylcarbamate. $C_{17}H_{25}NO_2$ (mw=275.39); MS: m/z (relative abundance) 275 (0.3), 219 (73.0), 202 (12.4), 174 (97.3), 158 (34.8), 146 (20.6), 132 (14.6), 57 (100).

2-(3-Methylphenyl)piperidine—A 1000 mL flask was charged with ethyl acetate 600 mL) and chilled to 5° C. Anhydrous hydrogen chloride gas (99%) was bubbled through the ethyl acetate for 15 minutes. The HCl feed was stopped, the ice bath removed, and the 2-(3-methylphenyl) piperidinyl-N-tert-butylcarbamate (59.5 g, 216 mmol) added. The solution was allowed to stir for 18 hours. Water (250 mL) was added to the solution. The layers were separated and the product was extracted into water (3×200 mL). The aqueous portion was adjusted to pH 14 with 45% (wt/v) potassium hydroxide. The product was extracted into ether (4×150 mL). The combined organic portions were dried ($MgSO_4$) and the solvent removed via rotary evaporation. Distillation under reduced pressure (75–90° C., 0.3 mmHg) provided 2-(3-methylphenyl)piperidine (10.4 g, 59.3 mmol, 27.5% yield); $C_{12}H_{17}N$ (mw=175.27); $^1H$ NMR: δ($CDCl_3$) 7.2–7.0 (m, 4H), 3.5 (m, 1H), 3.1 (m, 1H), 3.7 (t, 1H), 2.3 (s, 3H), 1.9–1.4 (m, 7H): $^{13}C$ NMR: δ($CDCl_3$) 145.4, 137.6, 128.0, 127.5, 127.0, 123.5, 62.1, 47.6, 34.8, 25.6, 25.3, 21.1; IR (capillary film) v 3319, 3267, 3022, 2924, 1932, 1855, 1777, 1680, 1441, 1323, 1108, 783, 701; MS: m/z (relative abundance) 175 (35.7), 160 (10.4), 146 (45.0), 132 (34.6), 118 (100), 91 (31.7)84 (48.4), 56 (7.7), 28 (23.3).

3,3,3-Trifluoropropyl(2-(3-methylphenyl)piperidinyl) dimethoxysilane—A 500 mL round bottomed flask was charged with tetrahydrofuran (300 mL) and isopropylmagnesium chloride (15 mL of a 2.0 M solution in THF, 30 mmol). The contents were cooled to 15° C. 2-(3-Methylphenyl)piperidine (34.3 mmol) was added over fifteen minutes via pressure equalizing addition funnel. The cold bath was removed and the contents stirred for two hours. 3,3,3-Trifluoropropyltrimethoxysilane (31.1 mmol) was added via pressure equalizing addition funnel. The contents were brought to reflux (65–70° C.) for two hours, and reaction progress was monitored by GC. Isolation was accomplished by removing the THF via rotary evaporation, taking the residue up in ether (250 mL), filtration and ether removal via rotary evaporation. Purification was accomplished by distillation to provide 3,3,3-trifluoropropyl(2-(3-methylphenyl)-piperidinyl)dimethoxysilane (24.1 mmol; 80.4% yield; b pt 101° C. at 0.2 mm Hg). $C_{17}H_{26}NO_2SiF_3$ (mw=361.47); MS: m/z (relative abundance) 361 (13.4), 332 (3.6), 270 (100), 174 (5.6), 155 (9.1), 125 (12.0), 105 (12.2), 59 (19.4).

Example IV 3,3,3-Trifluoropropyl(2-(3-methylphenyl)-pyrrolidinyl) dimethoxysilane (2-(3-Methylphenyl)-pyrrolidinyl)-N-tert-butylcarbamate—A 500 mL flask was charged with pyrrolidinyl-N-tert-butylcarbamate (17.3 g, 101 mmol), tetramethylethylenediamine (33 mL, 220 mmol), and THF (200 mL). The contents were cooled to −78° C. Sec-butyl lithium (93 mL of 1.3 M solution in cyclohexane, 120 mmol) was added over 15 minutes and the contents stirred at −78° C. for 3.5 hours. A 1000 mL flask was charged with THF (200 mL), 3-iodotoluene (25.7 mL, 7.00×10$^2$ mmol), copper (I) cyanide (0.896 g, 10.0 mmol), and bis-(triphenylphosphine)palladium chloride (3.5 g, 5.0 mmol). The contents were cooled to −78° C. The piperidinyl-N-tert-butylcarbamate anion was transferred into the iodotoluene solution via cannula. The reaction was allowed to stir for 18 hours and then heated to reflux (75° C.) for 18 hours. The contents were cooled and added to water (200 mL). The layers were separated and the aqueous layer was extracted with ether (2×150 mL). The combined organic portions were washed with brine (3×150 mL) and dried ($MgSO_4$). Removal of solvent by rotary evaporation provided 62.5 g of crude product. Distillation under reduced pressure (145° C., 0.2 mmHg) provided 2-(3-methylphenyl)pyrrolidinyl-N-tert-butylcarbamate (13.3 g, 50.9 mmol, 50% yield): $C_{16}H_{23}NO_2$ (mw=261.36).

2-(3-Methylphenyl)pyrrolidene—A 1000 mL flask was charged with ethyl acetate (600 mL) and chilled to 5° C. Anhydrous hydrogen chloride gas (99%) was bubbled through the ethyl acetate for 15 minutes. The HCl feed was stopped, the ice bath removed and the 2-(3-methylphenyl) pyrrolidinyl-N-tert-butylcarbamate (35.0 g, 134 mmol) was added. The solution was allowed to stir for 18 hours. Water (250 mL) was added, the layers separated, and the product extracted into water (3×200 mL). The aqueous portion was adjusted to pH 14 using 45% (wt/v) potassium hydroxide. The product was extracted into ether (4×150 mL). The combined organic portions were dried ($MgSO_4$) and the solvent removed via rotary evaporation. Distillation under reduced pressure (115–122° C., 2 mmHg) provided a 70:30 mixture of 2-(3-methylphenyl)-pyrrolidine and 2-(3-methylphenyl)pyrrolidene (14 g, 65% yield).

2-(3-Methylphenyl)pyrrolidine—A pressure reactor was charged with the olefin/product mixture (14 g), absolute ethyl alcohol (140 mL) and platinum oxide (2.8 g, 12 mmol). The reactor was filled with hydrogen (99.99%) to a pressure of 50 psig. The reaction mass stirred for 18 hours during which time the pressure decreased to 3 psig. The ethyl alcohol was removed by distillation under nitrogen. Distillation of the remainder under reduced pressure (63–74° C., 0.1 mmHg) provided 2-(3-methylphenyl)-pyrrolidine (10.8 g, 67 mmol, 77% yield, 97% purity); $C_{11}H_{15}N$ (mw= 161.24); $^1$H NMR: δ(CDCl$_3$) 7.3–6.9 (m, 4H), 4.1 (t, 1H), 3.1 (m, 1H), 2.9 (m, 1H), 2.3 (s, 3H), 2.1 (m, 1H), 1.9 (m, 3H), 1.6 (m, 1H); $^{13}$C NMR: δ(CDCl$_3$) 144.9, 137.9, 128.2, 127.5, 127.2, 123.6, 62.6, 47.0, 34.3, 25.6, 21.4; IR (capillary film) v 3327, 3014, 2953, 2866, 1937, 1861, 1783, 1399, 781, 709, MS: m/z (relative abundance) 160 (62.9), 146 (40.5), 132 (100), 118 (92.6), 92 (25.2), 70 (45.3), 43 (6.0), 28 (14.8).

3,3,3-Trifluoropropyl(2-(3-methylphenyl)pyrrolidinyl) dimethoxysilane—A 500 mL round bottomed flask was charged with tetrahydrofuran (300 mL) and isopropyl-magnesium chloride (20 mL of a 2.0 M solution in THF, 40 mmol). The contents were cooled to 15° C. 2-(3-Methylphenyl)pyrrolidine (39.1 mmol) was added over fifteen minutes via pressure equalizing addition funnel. The cold bath was removed and the contents stirred for two hours. 3,3,3-Trifluoropropyltrimethoxysilane (36.3 mmol) was added via pressure equalizing addition funnel. The contents were brought to reflux (65–70° C.) for two hours, and reaction progress was monitored by GC. Isolation was accomplished by removing the THF via rotary evaporation, taking the residue up in ether (250 mL), filtration and ether removal via rotary evaporation. Purification was accomplished by distillation to provide 3,3,3-trifluoropropyl(2-(3-methylphenyl)-pyrrolidinyl)dimethoxysilane (24.3 mmol; 62.2% yield). $C_{16}H_{24}NO_2SiF_3$ (mw=347.45) bp=128° C. at 0.2 mmHg; $^1$H NMR: (CDCl$_3$) δ 7.3–6.9 (m, 4H), 4.5 (t, 1H), 3.41 (s, 3H), 3.40 (s, 3H), 3.3 (t, 2H), 2.3 (s, 3H), 2.2–2.1 (m, 2H), 2.0–1.7 (m, 4H), 1.7–1.6 (m, 2H); $^{13}$C NMR: (CDCl$_3$) δ 147.8, 137.7, 128.1, 127.6 (quartet, J=275.9 Hz), 127.2, 126.8, 123.2, 61.7, 50.3, 47.4, 37.0, 34.3, 27.7 (quartet, J=30.1 Hz) 21.4, 3.0: MS: m/z (relative abundance) 347 (18.0), 318 (8.3), 304 (3.7), 256 (100), 155 (12.0), 125 (15.9), 59 (24.6).

Example V 3,3,3-Trifluoropropyl(cis-2,6-dimethylpiperidinyl) dimethoxysilane cis-2,6-Dimethylpiperidine—A 1000 mL round-bottomed flask was charged with 5M KOH (600 mL, 3 moles) and lutidine (15.0 g, 1.50×10$^2$ mmol). A solid aluminum/nickel alloy was added over 48 hours (1200 g). During the addition of the alloy, gas evolved and the internal temperature increased from 35° C. to 65° C. (no more than 15 g of the alloy was added in one portion). The salts were filtered through celite[1], and the filter cake washed with ether and water. The layers were separated. The product was extracted into ether (3×150 mL) and dried (MgSO$_4$), leaving crude 2,6-dimethylpiperidine (8.13 g, 71.2 mmol, 51% yield).

[1]CAUTION: A flammable Raney nickel type solid remains in the celite. This material will ignite in air if the filter cake dries. The solid is best neutralized by stirring it in a generous amount of dilute nitric acid for 48 hours.

3,3,3-Trifluoropropyl(cis-2,6-dimethylpiperidi-nyl)dimethoxysilane—A 500 mL round bottomed flask was charged with tetrahydrofuran (300 mL) and isopropyl-magnesium chloride (31 mL of a 2.0 M solution in THF, 62 mmol). The contents were cooled to 15° C. Cis-2,6-dimethylpiperidine (64 mmol) was added over fifteen minutes via pressure equalizing addition funnel. The cold bath was removed and the contents stirred for two hours. 3,3,3-Trifluoropropyltrimethoxysilane (57 mmol) was added via pressure equalizing addition funnel. The contents were brought to reflux (65–70° C.) for two hours, and reaction progress was monitored by GC. Isolation was accomplished by removing the THF via rotary evaporation, taking the residue up in ether (250 mL), filtration and ether removal via rotary evaporation. Purification was accomplished by distillation to provide 3,3,3-trifluoropropyl(cis-2,6-dimethylpiperidinyl)dimethoxysilane (27.4 mmol; 48% yield). $C_{12}H_{24}NO_2SiF_3$ (mw=299.40) bp=66° C. at 0.3 mmHg; $^1$NMR: (CDCl$_3$) δ 3.5 (s, 6H), 3.4–3.3 (m, 2H), 2.2–2.0 (m, 2H), 1.9–1.7 (m, 1), 1.6–1.4 (m, 5H), 1.2–1.0 (m, 6H), 0.8–0.7 (m, 2H); $^{13}$C NMR: (CDCl$_3$) δ 128 (quartet, J=275 Hz), 50.1, 44.2, 31.6, 28.3 (quartet, J=30 Hz), 24.6, 20.5, 14.3:MS: m/z (relative abundance) 299 (0.7), 284 (100), 202 (6.7), 155 (7.9), 98 (12.7), 59 (12.5).

Example VI 3,3,3-Trifluoropropyl(1,2,3,4-tetrahydroquinolinyl) dimethoxysilane—A 500 mL round bottomed flask was charged with tetrahydrofuran (300 mL) and isopropyl-magnesium chloride (30 mL of a 2.0 M solution in THF, 60 mmol). The contents were cooled to 15° C. 1,2,3,4-Tetrahydroquinoline (60 mmol) was added over fifteen minutes via pressure equalizing addition funnel. The cold bath was removed and the contents stirred for two hours. 3,3,3-Trifluoropropyltrimethoxysilane (54.5 mmol) was added via pressure equalizing addition funnel. The contents were brought to reflux (65–70° C.) for two hours and reaction progress was monitored by GC. Isolation was accomplished by removing the THF via rotary evaporation, taking the residue up in ether (250 mL), filtration and ether removal via rotary evaporation. Purification was accomplished by distillation to provide 3,3,3-trifluoropropyl(1,2,3,4-tetrahydroquinolinyl)dimethoxysilane (54 mmol; 99% yield). $C_{14}H_{20}NO_2SiF_3$ (mw=319.39) bp=110° C. at 0.35 mmHg; $^1$H NMR: (CDCl$_3$) δ 7.1–6.4 (m, 4H), 3.6–3.2 (m, overlapping with singlet, 8H), 2.9–2.7 (m 2H), 2.2–1.7 (m, 4H), 1.3–0.7 (m, 2H) $^{13}$C NMR: (CDCl$_3$) δ 130.2, 129.6, 128 (quartet, J=275 Hz), 126.8, 126.5, 119.2, 117.0, 50.5, 43.5, 27.8 (quartet, J=30 Hz), 23.8, 22.4, 3.4; MS: m/z (relative abundance) 319 (100), 222 (11.7), 190 (6.5), 182 (6.2) 155 (10.7), 132 (55.0), 125 (21.8), 117 (12.1), 59 (32.6).

Example VII 3,3,3-Trifluoropropyl(1,2,3,4-tetrahydroisoquinolinyl) dimethoxysilane—A 500 mL round bottomed flask was charged with tetrahydrofuran (300 mL) and isopropyl-magnesium chloride (30 mL of a 2.0 M solution in THF, 60 mmol). The contents were cooled to 15° C. 1,2,3,4-Tetrahydroisoquinoline (60 mmol) was added over fifteen minutes via pressure equalizing addition funnel. The cold bath was removed and the contents stirred for two hours. 3,3,3-Trifluoropropyltrimethoxysilane (54.5 mmol) was added via pressure equalizing addition funnel. The contents were brought to reflux (65–70° C.) for two hours and reaction progress was monitored by GC. Isolation was accomplished by removing the THF via rotary evaporation, taking the residue up in ether (250 mL), filtration and ether removal via rotary evaporation. Purification was accomplished by distillation to provide 3,3,3-trifluoropropyl(1,2,3,4-tetrahydroisoquinolinyl)dimethoxysilane (54 mmol; 99% yield). $C_{14}H_{20}NO_2SiF_3$ (mw=319.39) bp=98° C. at 0.3 mmHg; $^1$H NMR: (CDCl$_3$) δ 7.2–6.9 (m, 4H), 4.2–4.0 (d, 2H), 3.6–3.4 (s, 6H), 3.3–3.1 (dt, 2H), 2.8–2.6 (m, 2H), 2.2–1.9 (m, 2H), 0.9–0.8 (m, 2H); $^{13}$C NMR: (CDCl$_3$) δ 135.9, 135.1, 129.4, 128 (quartet J=275 Hz), 126.0, 125.9, 125.8, 50.4, 46.5, 42.1, 29.9, 28 (quartet, J=30 Hz), 2.8; MS: m/z (relative abundance) 319 (38.3), 318 (100), 222 (7.9), 132 (21.0), 104 (21.4), 79 (9.8), 59 (13.4).

Example VIII 3,3,3-Trifluoropropyl(decahydroquinolinyl) dimethoxysilane—A 500 mL round bottomed flask was charged with tetrahydrofuran (300 mL) and isopropylmagnesium chloride (28.75 mL of a 2.0 M solution in THF, 57.5 mmol). The contents were cooled to 15° C. Decahydroquinoline (57.5 mmol) was added over fifteen minutes via pressure equalizing addition funnel. The cold bath was removed and the contents stirred for two hours. 3,3,3-Trifluoropropyltrimethoxysilane (52.3 mmol) was added via pressure equalizing addition funnel. The contents were brought to reflux (65–70° C.) for two hours, and reaction progress was monitored by GC. Isolation was accomplished by removing the THF via rotary evaporation, taking the residue up in ether (250 mL), filtration and ether removal via rotary evaporation. Purification was accomplished by distillation to provide 3,3,3-trifluoropropyl (decahydroquinolyinyl)dimethoxysilane (53.1 mmol; quantitative yield). $C_{14}H_{26}NO_2SiF_3$ (mw=325.44) bp=103° C. at 1.0 mmHg; $^1H$ NMR: ($CDCl_3$) δ 3.5 (s, 6H), 3.1–2.7 (m, 3H), 2.2–1.9 (m, 3H), 1.8–1.1 (m, 12H), 0.9–0.7 (m, 2H); $^{13}C$ NMR ($CDCl_3$) δ 127.9 (quartet, J=275 Hz), 52.6, 50.4, 38.2, 36.9, 29.0, 28.5, 27.8 (quartet, J=30 Hz), 26.4, 26.3, 20.5, 3.1; MS: m/z (relative abundance) 325 (14.3), 282 (100), 228 (4.1), 125 (6.8), 96 (11.3), 59 (12.6).

Example IX 3,3,3-Trifluoropropyl(bis(2-ethylhexyl) aminodimethoxysilane—A 500 mL round bottomed flask was charged with tetrahydrofuran (300 mL) and isopropylmagnesium chloride (25 mL of a 2.0 M solution in THF, 50 mmol). The contents were cooled to 15° C. Bis(2-ethylhexyl)amine (50 mmol) was added over fifteen minutes via pressure equalizing addition funnel. The cold bath was removed and the contents stirred for two hours. 3,3,3-Trifluoropropyltrimethoxysilane (45 mmol) was added via pressure equalizing addition funnel. The contents were brought to reflux (65–70° C.) for two hours, and reaction progress was monitored by GC. Isolation was accomplished by removing the THF via rotary evaporation, taking the residue up in ether (250 mL), filtration and ether removal via rotary evaporation. Purification was accomplished by distillation to provide 3,3,3-trifluoropropyl bis(2-ethylhexyl) aminodimethoxysilane (44 mmol; 98% yield). $C_{21}H_{44}NO_2SiF_3$ (mw=427.66) bp=200° C. at 1.4 mmHg; $^1H$ NMR: ($CDCl_3$) δ 3.5 (s, 6H), 2.6–2.4 (dd, 4H), 2.2–2.0 (m, 2H), 1.6–1.1 (m, 18H), 1.0–0.7 (m, 14H); $^{13}C$ NMR: ($CDCl_3$) δ 128 (quartet, J=275 Hz), 50.4, 48.5, 39.4, 36.9, 30.8, 29.1, 28.2 (quartet, J=30 Hz), 23.2, 14.2, 10.3, 3.2; MS: m/z (relative abundance) 328 (100), 230 (25.6), 155 (7.4), 109 (2.9).

Example X

Polymerization Procedure

The aminosilane compounds of Examples I–IX were used as electron donors to polymerize propylene monomer. The polymerization reactor was heated to 70° C. and purged with a slow argon flow for 1 hour. The reactor was then pressurized up to 100 psig with argon at 70° C. and then vented. This procedure was repeated 4 more times. The reactor was then cooled to 30° C.

Separately, into an argon purged addition funnel was introduced in the following order: 75 mL of hexane, 4.47 mL of 1.5 M solution of triethylaluminum (TEAL) (0.764 g, 0.0067 mol) in hexane, approx. 3.4 mL of 0.1 M solution of the aminosilane electron donors (0.00034 mol) of Examples I–IX and allowed to stand for 5 minutes. Of this mixture, 35 mL was added to a flask. Then 0.0129 g of FT4S solid catalyst component (a titanium halide and electron donor supported on an active $MgCl_2$ compound catalyst component commercially available from Montell Italia SpA) was added to the flask and mixed by swirling for a period of 5 minutes. The catalytic complex thus obtained was introduced, under an argon purge, into the above polymerization reactor at room temperature. The remaining hexane/TEAL/silane solution was then drained from the addition funnel to the flask, the flask was swirled and drained into the reactor and the injection valve was closed.

The polymerization reactor was slowly charged with 2.2 L of liquid propylene, while agitating, and 0.25 mole percent of $H_2$. Then the reactor was heated to 70° C. and polymerization was commenced for about 2 hours at constant temperature and pressure. After about 2 hours agitation was stopped and the remaining propylene was slowly vented. The reactor was heated to 80° C., purged with argon for 10 minutes and then cooled to room temperature and opened. The polymer was removed and dried in a vacuum oven at 80° C. for 1 hour before testing was performed.

Unless otherwise specified, the intrinsic viscosity of the polymers, IV, is measured in decalin at 135° C. using a Ubbelohde type viscometer tube by the method of J. H. Elliot et al., *J. Applied Polymer Sci.*, 14, 2947–63 (1970). The mileage of the polymer is calculated according to the formula:

$$\text{mileage} = \frac{\text{grams of polypropylene}}{\text{grams of catalyst}}$$

The percent xylene solubles at room temperature, % XSRT, of the polymer was determined by dissolving 2 g of polymer in 200 ml of xylene at 135° C., cooling in a constant temperature bath at 22° C. and filtering through fast filter paper. An aliquot of the filtrate was evaporated to dryness, the residue weighed and the weight % soluble fraction calculated.

Test results are set forth in Table 1 below.

TABLE 1

| Aminosilane | % Hydrogen | Mileage (g pp/g cat) | Intrinsic Viscosity (dL/g) | Melt Flow Rate | XSRT (wt %) | P.I. |
|---|---|---|---|---|---|---|
| Example I | 0 | 22,353 | 4.94 | 0 | 2.19 | |
| | 0.2 | 47,168 | 3.7 | 0.56 | 3.03 | 5.6 |
| | 0.75 | 57,767 | 2.63 | 3.18 | 1.93 | |
| | 1.5 | 56,486 | 1.83 | 12.49 | 2.57 | 4.5 |
| | 2.5 | 55,208 | 1.57 | 31.27 | 2.31 | 4.6 |
| | 5 | 54,222 | 1.16 | 98.89 | 2.6 | 4.6 |
| Example II | 0 | 21,329 | 9.4 | 0.02 | 2.79 | |
| | 0.2 | 45,487 | 3.48 | 0.75 | 2.21 | 5.5 |

TABLE 1-continued

| Aminosilane | % Hydrogen | Mileage (g pp/g cat) | Intrinsic Viscosity (dL/g) | Melt Flow Rate | XSRT (wt %) | P.I. |
|---|---|---|---|---|---|---|
| | 0.75 | 57,714 | 2.4 | 4.29 | 2.18 | |
| | 1.5 | 54,528 | 1.82 | 12.66 | 2.47 | 5.2 |
| | 2.5 | 53,555 | 1.48 | 34.54 | 2.79 | 4.9 |
| | 5 | 56,153 | 1.25 | 96.27 | 2.75 | 4.6 |
| Example III | 0 | 19,805 | 6.47 | 0.01 | 3.39 | |
| | 0.2 | 43,750 | 2.39 | 4.3 | 2.45 | 5.0 |
| | 0.75 | 51,386 | 1.56 | 25.23 | 2.24 | |
| | 1.5 | 46,818 | 1.22 | 88.09 | 2.74 | 4.4 |
| | 2.5 | 43,297 | 1.01 | 213.06 | 2.86 | 4.4 |
| Example IV | 0 | 20,952 | 11.1 | 0.01 | 3.43 | |
| | 0.2 | 47,211 | 2.78 | 1.6 | 2.1 | 4.8 |
| | 0.75 | 52,444 | 1.95 | 9.03 | 2.42 | |
| | 1.5 | 49,285 | 1.54 | 30.43 | 2.42 | 4.5 |
| | 2.5 | 46,333 | 1.22 | 77.65 | 2.15 | 4.4 |
| | 5 | 42,755 | 0.91 | 307.31 | 2.85 | 4.5 |
| Example V | 0 | 14,601 | 7.72 | 0.03 | 5.15 | |
| | 0.2 | 33,465 | 2.28 | 5.04 | 3.5 | 6.6 |
| | 0.75 | 41,456 | 1.58 | 25.3 | 2.87 | |
| | 1.5 | 42,391 | 1.26 | 75.38 | 2.95 | 4.5 |
| | 2.5 | 42,173 | 1.11 | 153.6 | 3 | 4.7 |
| Example VI | 0 | 18,216 | 6.12 | 0.03 | 4.49 | |
| | 0.2 | 45,398 | 2.04 | 6.82 | 2.85 | 4.5 |
| | 0.75 | 54,857 | 1.5 | 29.56 | 2.77 | |
| | 1.5 | 46,923 | | 74.7 | 2.94 | 4.3 |
| | 2.5 | 48,620 | | 96.4 | 2.85 | 4.3 |
| | 5 | 42,058 | | 551 | 2.97 | 4.4 |
| Example VII | 0 | 17,939 | 6.88 | 0.03 | 3.37 | |
| | 0.2 | 37,804 | 2.05 | 14.2 | 2.55 | 4.4 |
| | 0.75 | 44,151 | 1.47 | 32.63 | 2.45 | |
| | 1.5 | 37,378 | | 101.4 | 2.64 | 4.3 |
| | 2.5 | 39,754 | | 149.3 | 2.41 | 4.3 |
| | 5 | 36,090 | | 694.8 | 2.83 | 4.2 |
| Example VIII | 0 | 19,000 | 10.23 | 0.01 | 2.95 | |
| | 0.2 | 40,280 | 2.57 | 2.77 | 2.15 | N.D.* |
| | 0.75 | 47,407 | 1.93 | 11.75 | 2.2 | |
| Example IX | 0 | 19,655 | 5.16 | 0.11 | 8.27 | |
| | 0.2 | 36,272 | 2.08 | 13.24 | 7.29 | 4.4 |
| | 0.75 | 40,540 | 1.21 | 75 | 5.94 | |
| | 1.5 | 38,867 | | 179.1 | 5.86 | 4.6 |
| | 2.5 | 36,581 | | 344.4 | 8.48 | 4.5 |
| | 5 | 33,966 | | 1,598 | 6.55 | 4.4 |

*N.D. - Not Done

Comparative Example

The polymerization procedure of Example X was followed, using 0.25% of hydrogen and a 20/1 ratio of Al/Si, and with 3,3,3-trifluoropropyl(4-methylpiperidyl)-dimethoxysilane used as the aminosilane. The catalyst exhibited a mileage of 43,900 grams of polypropylene per gram of catalyst. The resulting polymer had an intrinsic viscosity of 2.35, a XSRT of 1.51% and a polydispersity index of 4.22.

Other features, advantages and embodiments of the invention disclosed herein will be readily apparent to those exercising ordinary skill after reading the foregoing disclosures. In this regard, while specific embodiments of the invention have been described in considerable detail, variations and modifications of these embodiments can be effected without departing from the spirit and scope of the invention as described and claimed.

What is claimed is:

1. An aminosilane of the following formula:

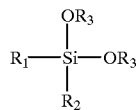

wherein $R_1$ is a linear or branched $C_{1-22}$ alkyl or $C_{3-22}$ cycloalkyl, which is substituted with at least one halogen atom;

$R_2$ is a bis(linear or branched $C_{1-22}$ alkyl or $C_{3-22}$ cycloalkyl)amino, a substituted piperidinyl, a substituted pyrrolidinyl, decahydroquinolinyl, 1,2,3,4-tetrahydroquinolinyl or 1,2,3,4-tetrahydroisoquinolinyl, with the substituent selected from the group consisting of linear or branched $C_{1-8}$ alkyl, phenyl, phenyl substituted with linear or branched $C_{1-8}$ alkyl and trimethylsilyl, with the proviso that when the substituent is $C_{1-8}$ alkyl, there must be at least two such substituent groups present; and $R_3$ is a linear or branched $C_{1-8}$ alkyl or $C_{3-8}$ cycloalkyl.

2. The aminosilane of claim 1, wherein $R_1$ is 3,3,3-trifluoro-propyl.

3. The aminosilane of claim 2, wherein $R_3$ is methyl or ethyl.

4. The aminosilane of claim 3, wherein $R_2$ is a bis(linear or branched $C_{1-22}$ alkyl or $C_{3-22}$ cycloalkyl)amino.

5. The aminosilane of claim 4, wherein $R_2$ is bis(2-ethylhexyl) amino.

6. The aminosilane of claim 3, wherein $R_2$ is decahydroquinolinyl.

7. The aminosilane of claim 3, wherein $R_2$ is 1,2,3,4-tetrahydro-quinolinyl.

8. The aminosilane of claim 3, wherein $R_2$ is 1,2,3,4-tetrahydro-isoquinolinyl.

9. The aminosilane of claim 3, wherein $R_2$ is 2-trimethylsilyl-piperidinyl.

10. The aminosilane of claim 3, wherein $R_2$ is 2-(3-methylphenyl)piperidinyl.

11. The aminosilane of claim 3, wherein $R_2$ is cis-2,6-dimethyl-piperidinyl.

12. The aminosilane of claim 3, wherein $R_2$ is 2-trimethylsilyl-pyrrolidinyl.

13. The aminosilane of claim 3, wherein $R_2$ is 2-(3-methylphenyl)pyrrolidinyl.

14. A catalyst for the polymerization of olefins, comprising the reaction product of:
(A) an aluminum alkyl compound;
(B) an aminosilane compound of the formula

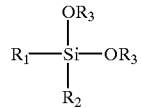

wherein
$R_1$ is a linear or branched $C_{1-22}$ alkyl or $C_{3-22}$ cycloalkyl, which is substituted with at least one halogen atom;
$R_2$ is a bis(linear or branched $C_{1-22}$ alkyl or $C_{3-22}$ cycloalkyl)amino, a substituted piperidinyl, a substituted pyrrolidinyl, decahydroquinolinyl, 1,2,3,4-tetrahydroquinolinyl or 1,2,3,4-tetrahydroisoquinolinyl, with the substituent selected from the group consisting of linear or branched $C_{1-8}$ alkyl, phenyl, phenyl substituted with linear or branched $C_{1-8}$ alkyl and trimethylsilyl, with the proviso that when the substituent is $C_{1-8}$ alkyl, there must be at least two such substituent groups present must contain halogen; and
$R_3$ is linear or branched $C_{1-8}$ alkyl or $C_{3-22}$ cycloalkyl; and
(C) a solid component comprising a titanium compound having at least one titanium-halogen bond and an electron donor, both supported on an activated anhydrous magnesium dihalide.

15. The catalyst of claim 14, wherein said aluminum alkyl compound is triethyl aluminum, and said solid component comprises the reaction product of titanium tetrachloride, active magnesium chloride and an electron donor.

16. An aminosilane of the following formula:

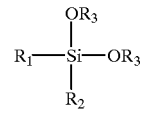

wherein $R_1$ is 3,3,3-trifluoro-propyl;

$R_2$ is decahydroquinolinyl, 1,2,3,4-tetrahydro-quinolinyl or 1,2,3,4-tetrahydro-isoquinolinyl; and $R_3$ is methyl or ethyl.

* * * * *

UNITED STATES PATENT AND TRADEMARK OFFICE
CERTIFICATE OF CORRECTION

PATENT NO. : 6,130,180
DATED : October 10, 2000
INVENTOR(S) : Constantine Stewart et al.

It is certified that error appears in the above-identified patent and that said Letters Patent is hereby corrected as shown below:

Column 7,
Line 48, change "4.4" to -- -4.4 --

Column 18,
Lines 9 and 10, delete "must contain halogen"
Line 11, change "$C_{3-22}$" to -- $C_{3-8}$ --

Signed and Sealed this

Eighth Day of July, 2003

JAMES E. ROGAN
*Director of the United States Patent and Trademark Office*